United States Patent
Seebo

(10) Patent No.: US 8,713,850 B2
(45) Date of Patent: May 6, 2014

(54) ALGAE HIGH DENSITY BIOREACTOR

(76) Inventor: H. Freeman Seebo, Seattle, WA (US)

( * ) Notice: Subject to any disclaimer, the term of this patent is extended or adjusted under 35 U.S.C. 154(b) by 206 days.

(21) Appl. No.: 12/650,382

(22) Filed: Dec. 30, 2009

(65) Prior Publication Data

US 2010/0162621 A1   Jul. 1, 2010

Related U.S. Application Data

(60) Provisional application No. 61/203,860, filed on Dec. 30, 2008.

(51) Int. Cl.
*A01G 7/00* (2006.01)
*A01G 7/02* (2006.01)

(52) U.S. Cl.
USPC .......................................... 47/1.4; 435/292.1

(58) Field of Classification Search
USPC .......... 47/1.4; 435/291.4, 294.1, 297.5, 292.1
See application file for complete search history.

(56) References Cited

U.S. PATENT DOCUMENTS

| | | | | |
|---|---|---|---|---|
| 3,102,082 | A * | 8/1963 | Brewer | 435/30 |
| 3,413,124 | A * | 11/1968 | Cavit | 426/11 |
| 3,955,317 | A * | 5/1976 | Gudin | 435/420 |
| 3,959,923 | A | 6/1976 | Selke | |
| 4,253,271 | A | 3/1981 | Raymond | |
| 4,937,196 | A * | 6/1990 | Wrasidlo et al. | 435/297.2 |
| 5,981,271 | A * | 11/1999 | Doucha et al. | 435/292.1 |
| 6,228,607 | B1 * | 5/2001 | Kersten et al. | 435/41 |
| 6,370,815 | B1 | 4/2002 | Skill et al. | |
| 6,468,792 | B1 * | 10/2002 | Bader | 435/325 |
| 6,509,188 | B1 * | 1/2003 | Trosch et al. | 435/292.1 |
| 7,176,024 | B2 | 2/2007 | Branson et al. | |
| 7,536,827 | B2 | 5/2009 | Busch et al. | |
| 2004/0077075 | A1 * | 4/2004 | Jensen et al. | 435/297.2 |
| 2007/0289206 | A1 * | 12/2007 | Kertz | 47/1.4 |

FOREIGN PATENT DOCUMENTS

| | | | | |
|---|---|---|---|---|
| JP | 63233779 A | * | 9/1988 | C12M 3/04 |
| WO | WO 8804316 A1 | * | 6/1988 | C12M 1/00 |
| WO | WO 2006122088 A1 | * | 11/2006 | |

* cited by examiner

*Primary Examiner* — David Parsley
*Assistant Examiner* — Danielle Clerkley
(74) *Attorney, Agent, or Firm* — Thomas E. Loop

(57) ABSTRACT

The invention disclosed herein relates to an ultra high intensity micro algal bioreactor designed to minimize the area foot print while completely controlling and optimizing the conditions for growing one or more specific strains of micro algae at maximum efficiency and minimum cost. The innovative bioreactor is in the form of an algae growing assembly that comprises a plurality of growing trays vertically stacked together and retained within a transparent housing. Each growing tray is configured to flowingly transport nutrient enriched water to the growing tray positioned immediately beneath it. Each growing tray is composed of a stiff transparent plastic sheet having a pliable transparent gas permeable membrane affixed thereon. A carbon dioxide gas infusion system is fluidicly connected to each of the plurality of growing trays such that carbon dioxide gas is able to (1) inflate respective carbon dioxide gas chambers, and (2) diffuse into the nutrient enriched water.

3 Claims, 4 Drawing Sheets

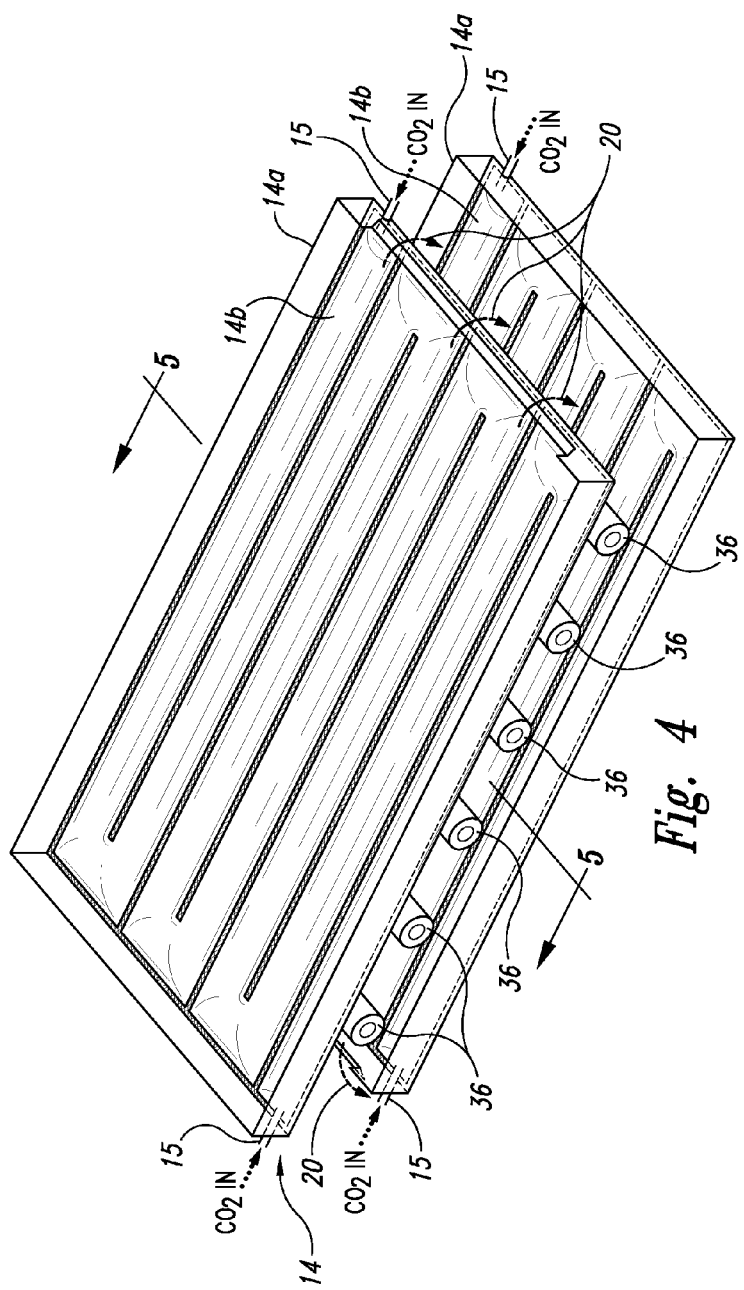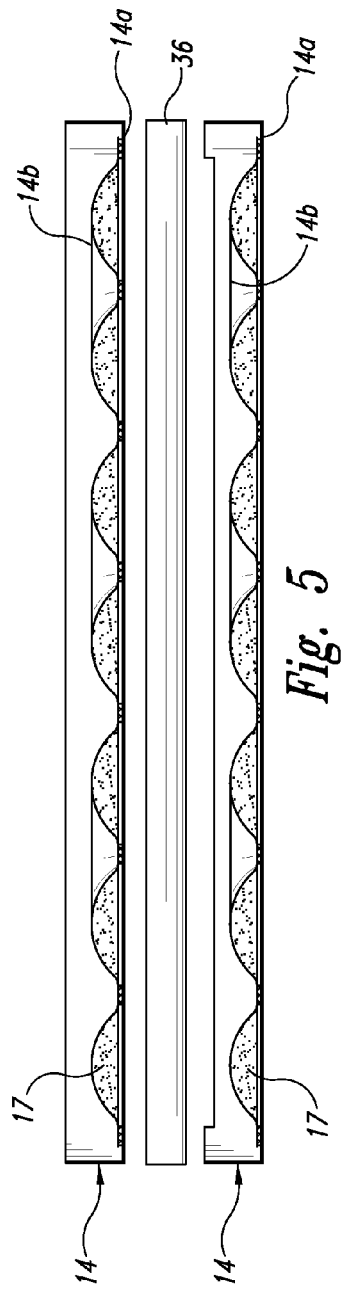

ALGAE HIGH DENSITY BIOREACTOR

CROSS-REFERENCE TO RELATED APPLICATIONS

This application claims the benefit of U.S. Provisional Application No. 61/203,860 filed on Dec. 30, 2008, which application is incorporated herein by reference in its entirety for all purposes.

TECHNICAL FIELD

The present invention relates generally to bioreactors and, more particularly, to algae growing bioreactors, assemblies and related systems for growing and cultivating algae and/or other micro-organisms.

BACKGROUND OF THE INVENTION

Algae has long been viewed as a nuisance and is often referred to as "pond scum." However, it has also been known that micro algae can be a major resource. Spirulina, for instance, is noted as the food resource with the highest level of digestible protein of any plant source. Other species, of which there are many, are sources of medicines, dyes, alcohols, and lipids as well as proteins. Recently, with the concern over various issues related to fossil fuels, micro algae with its propensity for creating lipids (in some species 30% to 50% or more by weight) has become the focus of a renewable source for biodiesel.

The growth of algae depends on the nutrients in the water as well as the illumination that is available for producing photosynthesis. Nutrients for algae are developed, for example, as oxidation products in wastewater and sewage treatment plants operating with aeration. Algae take up these oxidation products, and the water is softened as well as disinfected. Thus, utilization of algae for purposes of water purification is a viable alternative for chemical removal of oxidation products. Water purified by algae can readily be recycled into the water supply.

Many parts of the world, particularly in higher latitudes with prevailing unfavorable weather conditions do not offer sufficient natural light to permit cleaning and clearing of water by means of growing algae. Instead, artificial light is needed at least as a supplement. Generally speaking, photochemical effectiveness of light increases with its intensity within a certain range, while for higher intensities one approaches a saturation level so that further increases in light intensity do not produce any gain in photochemical effectiveness.

Prior mass algae growing systems have yet to prove economical because (1) they require relatively deep containment (20-100 cm) in order to provide for temperature control; (2) they produce comparatively dilute cultures; (3) they make inefficient use of carbon dioxide and little use of direct sunlight; (4) they require substantial energy inputs to provide mixing to avoid thermal stratification; (5) they must process larger volumes of water to obtain the same harvest yields of algal matter that might be collectible from shallower systems; and (6) they permit little or no control and/or regulation of those environmental elements which control and regulate the performance characteristics of the cultured cells.

Accordingly, there is a need in the art for new and improved algae growing and cultivating systems. The present invention fulfills this need and provides for further related advantages.

SUMMARY OF THE INVENTION

In brief, the present invention relates to an ultra high intensity micro algal bioreactor designed to minimize the area foot print while completely controlling and optimizing the conditions for growing one or more specific strains of micro algae at maximum efficiency and minimum cost. The invention optimizes the algal exposure to light, natural and artificial, and maintains optimum water temperature while allowing the maximum absorption of carbon dioxide while cleaning sewage and other organic waste water streams of nutrients for the benefit of a sustainable environment, as well as an economic benefit to all stakeholders.

The present invention is also more specifically directed to an algae growing assembly for growing and cultivating algae. In one embodiment, the algae growing assembly comprises: a plurality of growing trays vertically stacked together and retained within a transparent housing, wherein each growing tray is configured to flowingly transport nutrient enriched water to one of the plurality of growing trays positioned immediately beneath it; a plurality of lights positioned in between the plurality of growing trays and within the transparent housing; and a carbon dioxide gas infusion system for adding carbon dioxide gas to the nutrient enriched water contained within each of the plurality of growing trays. Each of the plurality of growing trays may be characterized in that each is composed of a rigid or semi-rigid transparent plastic sheet having a pliable transparent gas permeable membrane affixed thereon. The rigid or semi-rigid transparent plastic sheet and the pliable transparent gas permeable membrane affixed thereon define, in the space between them, an inflatable carbon dioxide gas chamber, and wherein the carbon dioxide gas infusion system is fluidicly connected to each of the plurality of growing trays such that carbon dioxide gas is able to (1) inflate the carbon dioxide gas chamber of each of the plurality of growing trays, and (2) diffuse into the nutrient enriched water contained within each of the plurality of growing trays.

Objects of the invention include, but are not limited to: (1) intensification of the growing area to achieve maximum yield at a low cost; (2) dependable recovery of carbon dioxide from digesters and exhaust streams; (3) simplicity of structure and design so as to be feasible whether located on a farm, or in the heart of intensive population centers; (4) control of light and temperature for positive yield; (5) cleaning of water streams that have heretofore been considered contamination of natural water resources such as aquifers, streams, rivers, estuaries, ponds, lakes, seas and oceans; and (6) contributing to sustainable environments and economic feasibility.

These and other aspects of the present invention will become more readily apparent to those possessing ordinary skill in the art when reference is made to the following detailed description in conjunction with the accompanying drawings.

BRIEF DESCRIPTION OF THE DRAWINGS

The drawings are intended to be illustrative and symbolic representations of certain exemplary embodiments of the present invention and as such they are not necessarily drawn to scale. In addition, it is to be expressly understood that the relative dimensions and distances depicted in the drawings (and described in the "Detailed Description of the Invention" section) are exemplary and may be varied in numerous ways. Finally, like reference numerals have been used to designate like features throughout the several views of the drawings.

FIG. 4 is a side elevational view of first and second growing trays positioned one on top of the other in accordance with an embodiment of the present invention, and wherein the gas permeable membrane is inflated.

FIG. 5 is a side cross-sectional view of the first and second growing trays positioned one on top of the other taken along line 5-5 of FIG. 4.

DETAILED DESCRIPTION OF THE INVENTION

Figure 1:
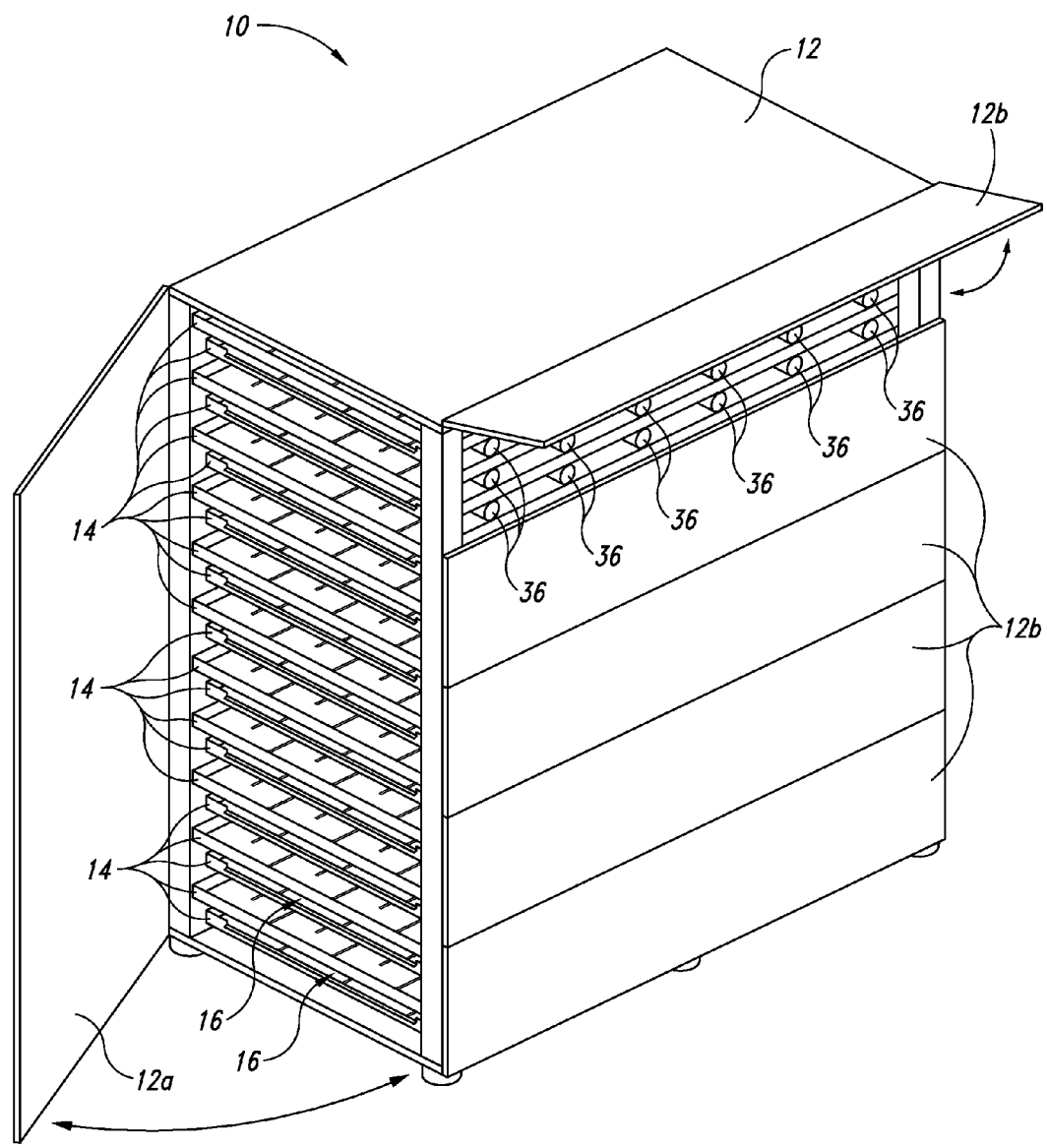
FIG. 1 illustrates a side elevational view of an algae growing assembly in accordance with an embodiment of the present invention.
Figure 2:
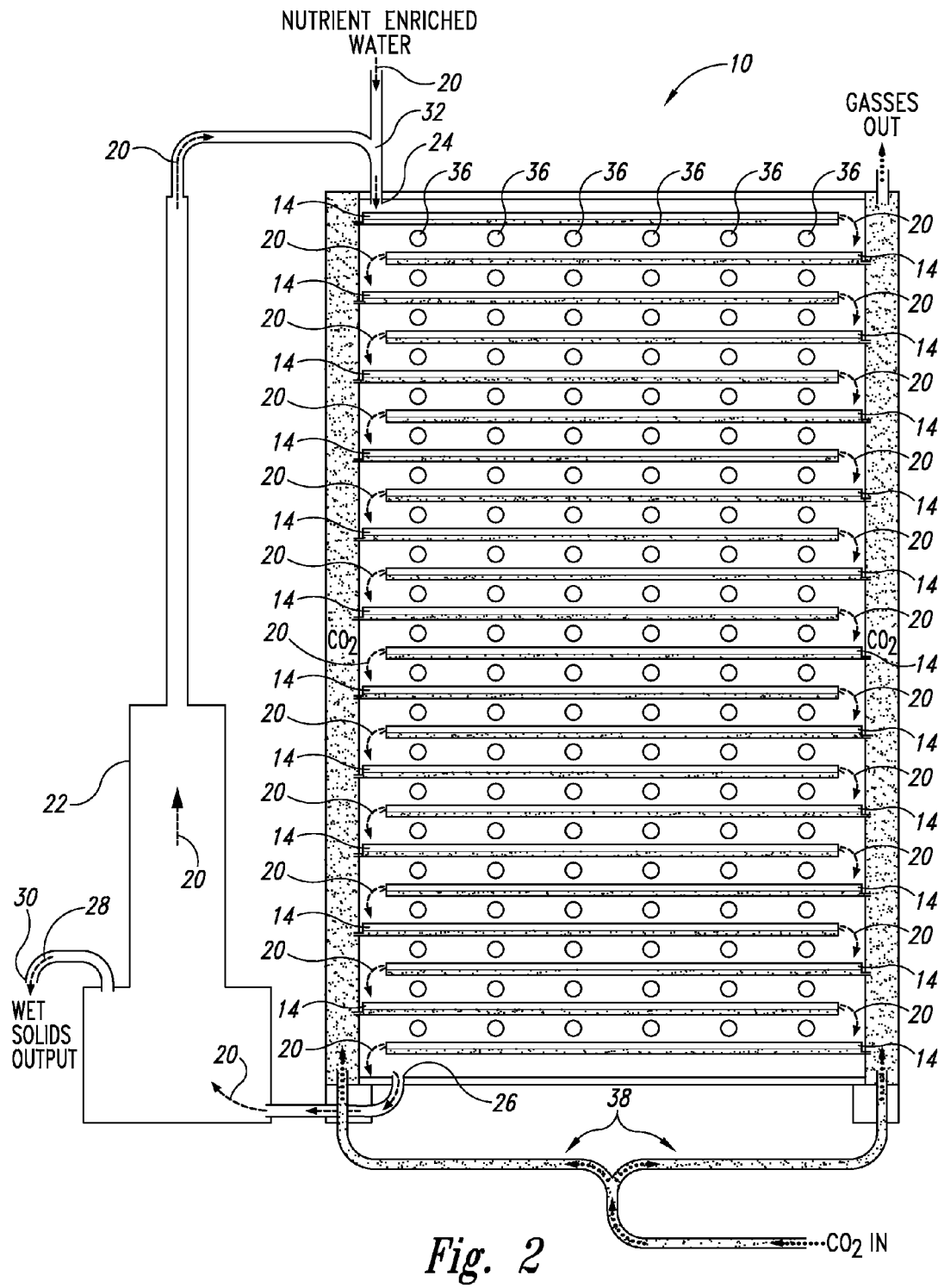
FIG. 2 illustrates a side cross-sectional view of an algae growing assembly in accordance with an embodiment of the present invention.

Referring now to the drawings wherein like references numerals have been used to designate like or corresponding elements, and more particularly to FIGS. 1 and 2, the present invention in one embodiment is directed to an algae growing assembly 10. As shown, the algae growing assembly 10 comprises a transparent housing structure 12 (having a front door 12a and a plurality of openable side panels 12b) and configured to retain a plurality of vertically stacked algae growing trays 14. Each growing tray 14 is removable and includes a spillway 16 positioned at one end 18. Each growing tray is configured to flowingly transport nutrient enriched water 20 (not directly shown but depicted as dashed lines in FIG. 2) from one growing tray 14 to the growing tray 14 positioned immediately beneath it. More specifically, the plurality of vertically stacked algae growing trays 14 are each positioned such that the spillway 16 of one growing tray 14 is opposite from the spillway 16 of the growing tray 14 positioned both immediately beneath and above it. In this configuration and as shown, the nutrient enriched water 20 is able to gravity flow across each growing tray 14 and spill into the growing tray 14 positioned immediately beneath it. Thus, the nutrient enriched water 20 (that contains algae) is able to flow in a zigzag manner throughout the algae growing assembly 10.

As best shown in FIG. 2, a centrifugal pump filter unit 22 is used to pump, filter, and re-circulate the nutrient enriched water 20. The nutrient enriched water 20 is first fed (together with seed algae or other suitable microorganism) into the algae growing assembly 10 by way of an inlet portal 24 positioned above the upper most growing tray 14. The nutrient enriched water 20 is then allowed to gravity flow in a zigzag manner throughout the algae growing assembly 10, and exit therefrom by way of an outlet portal 26 positioned at the bottom of the algae growing assembly 10 (and is then reintroduced back into the centrifugal pump filter unit 22). The centrifugal pump filter unit 22 processes the nutrient enriched water 20 so as (1) to remove accumulated wet solids 28 by way of a second outlet portal 30, and (2) to re-circulate the remaining nutrient enriched water 20 back to the top of the algae growing assembly 10. The remaining nutrient enriched water 20 is mixed with selected amounts of fresh nutrient enriched water 20 that is introduced into the system at a mixing zone 32.

Figure 3A:
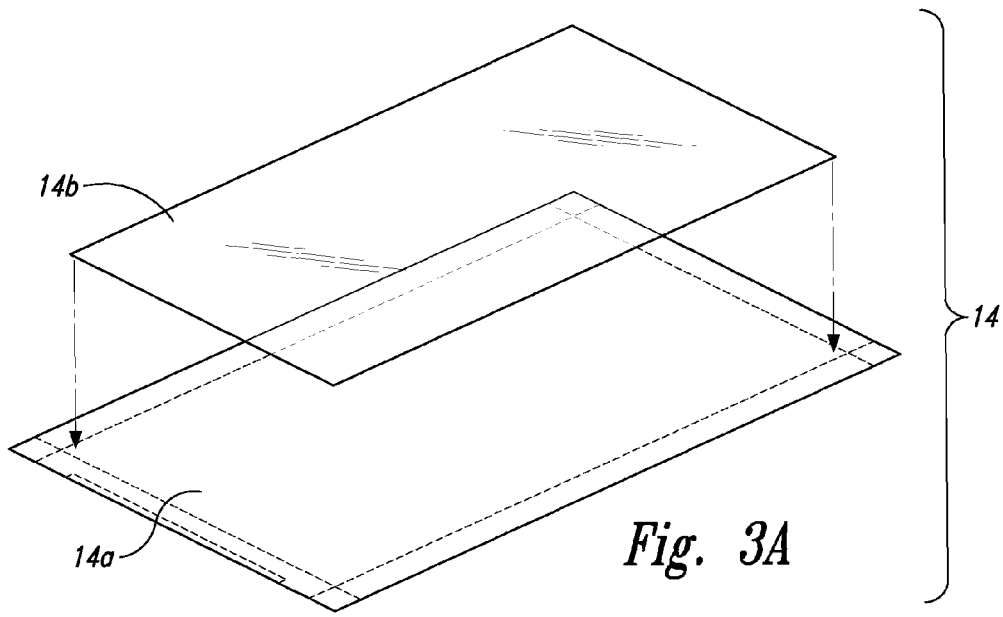
FIG. 3A is an exploded side elevational view of an unfolded growing tray and its corresponding gas permeable membrane in accordance with an embodiment of the present invention.
Figure 3B:
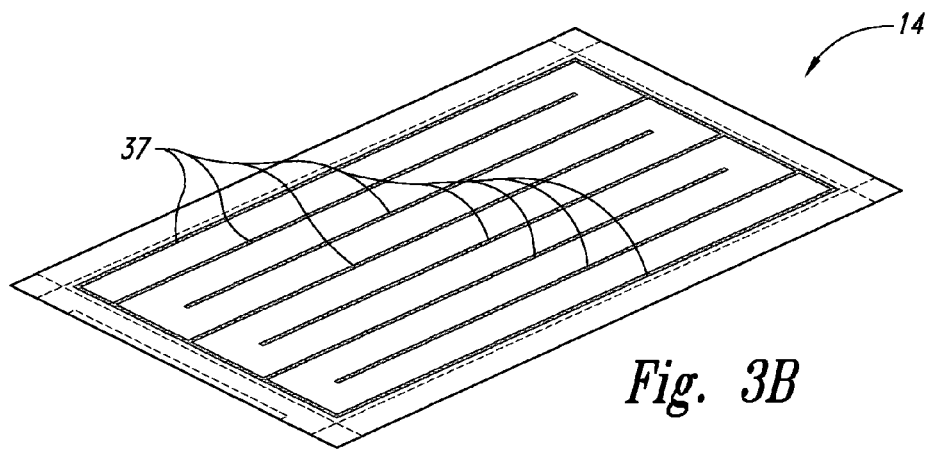
FIG. 3B is a side elevational view of an unfolded growing tray together with a corresponding gas permeable membrane in accordance with an embodiment of the present invention, wherein the gas permeable membrane is positioned on top of the unfolded growing tray while being held in place by one or more glue lines.
Figure 3C:
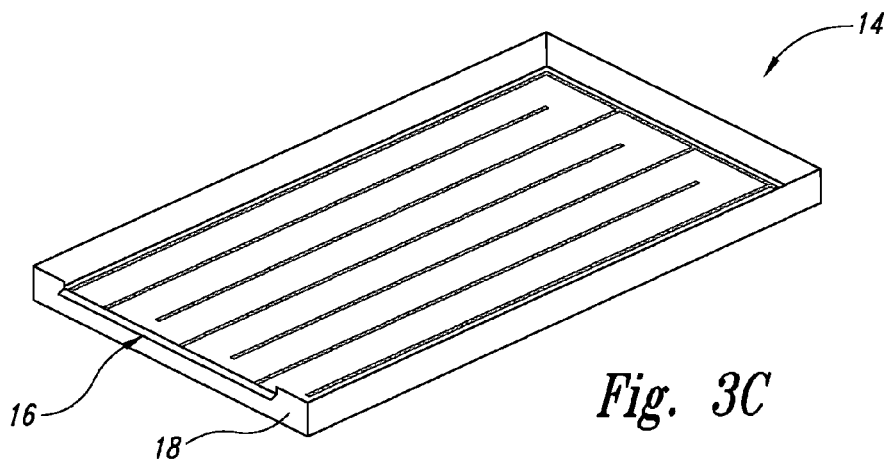
FIG. 3C is a side elevational view of a folded growing tray together with a corresponding gas permeable membrane in accordance with an embodiment of the present invention, wherein the gas permeable membrane is positioned on top of the folded growing tray while being held in place by one or more glue lines.

An important and novel aspect of the above-described algae growing assembly 10 resides in the construction and configuration of each of the plurality of vertically stacked algae growing trays 14. More specifically, and with reference to FIGS. 3A-C, each growing tray 14 comprises a rigid or semi-rigid transparent sheet 14a such as, for example, a polycarbonate or PLEXIGLASS, that has a gas permeable membrane 14b bonded thereon. In this regard, FIGS. 3A-C illustrates an exploded side elevational view of a rigid or semi-rigid transparent sheet 14a and its corresponding gas permeable membrane 14b in accordance with an embodiment of the present invention. As best shown in FIG. 3B, the gas permeable membrane 14b is positioned on top of the rigid or semi-rigid transparent sheet 14a and is held in place by one or more glue lines 37. Thus, FIG. 3B illustrates a side elevational view of an "unfolded" growing tray 14. As best shown in FIG. 3C, the unfolded growing tray 14 is subsequently cut and folded to form an algae growing tray 14 having a spillway 16 positioned at one end 18. As shown, the glue lines 37 of each of the plurality of growing trays 14 are positioned so as to form a serpentine path for subsequent $CO_2$ infusion into the system (described below).

In order to promote and enhance photosynthesis, the algae growing assembly 10 also includes a plurality of lights 36 and a carbon dioxide ($CO_2$) infusion system 38. As shown and in a preferred embodiment, the plurality of lights 36 are a series of tube lights uniformly positioned above and below each of the plurality of vertically stacked algae growing trays 14 (except that there are no tube lights positioned above the upper most growing tray or below the bottom most growing tray—as shown). The plurality of lights 36 may be configured to be turned on and off intermittently and for selected durations. The $CO_2$ infusion system 38 includes a pump (not shown) that pumps $CO_2$ into opposite ends of each of the growing trays 14 by way of $CO_2$ inlet portals 15 (as best shown in FIG. 4). In this configuration, $CO_2$ is able to be pumped into each of the plurality of growing trays 14 so as to inflate the space between the rigid or semi-rigid transparent sheet 14a and its corresponding gas permeable membrane 14b. Because the gas permeable membrane 14b allows the escape or infusion of $CO_2$ into the nutrient enriched water 20 when under positive pressure, the nutrient enriched water 20 is further enriched with $CO_2$ during operation.

Stated somewhat differently, each of the plurality of growing trays 14 is composed of a rigid or semi-rigid transparent plastic sheet 14a having a pliable transparent gas permeable membrane 14b affixed thereon. As best shown in FIG. 5, the rigid or semi-rigid transparent plastic sheet 14a and the pliable transparent gas permeable membrane 14b affixed thereon define, in the space between them, an inflatable carbon dioxide gas chamber 17. The carbon dioxide gas infusion system 38 is fluidicly connected to each of the plurality of growing trays (by way of tubing not shown for purposes of simplicity) such that carbon dioxide gas is able to (1) inflate the carbon dioxide gas chamber 17 of each of the plurality of growing trays 14, and (2) diffuse into the nutrient enriched water 20 contained within each of the plurality of growing trays 14. Each of the plurality of growing trays 14 generally also further comprises one or more glue lines positioned 37 along at least the outer edges of the pliable transparent gas permeable membrane 14b and between the rigid transparent plastic sheet 14a and the pliable transparent gas permeable membrane 14b. The one or more glue lines 37 define a serpentine path within each of the respective inflatable carbon dioxide gas chambers 17 (associated with each of the plurality of growing trays 14).

The algae growing assembly 10 is scalable. The transparent housing structure 12 and each of the plurality of vertically stacked algae growing trays 14 are preferably made (at least in part) of a rigid or semi-rigid transparent material such as, for example, a polycarbonate or PLEXIGLASS, to thereby maximize exposure of the algae to light, both natural and artificial. In order to facilitate For purposes of illustration and not restriction, the following Example demonstrates various aspects and utility of the present invention as conceived and contemplated by the inventor.

EXAMPLE

Each stack preferably contains 24 trays that are 3.25 inches deep (with a 0.25 inch spillway) by 12 feet long by 6 feet wide. Each tray (made of transparent material such as a clear plastic) may be directly connected to three of the four walls of the "transparent housing." The fourth side of tray is preferably built with a 3 inch face and a lip (i.e., spillway) to allow the seeded algae growth media to spill down to the next level and so on. Each tray is reversed from the one immediately above it so that there is both light access to the tray above and the one below, and simultaneously to maximize the absorption of $CO_2$ that is introduced into the structure and to minimize the footprint while optimizing the concentration of growth media. Each such stack may occupy approximately 82 square feet of surface area, and may have the equivalent productive area of approximately 6,712 square feet of pond.

The apparatus as shown is represented as a rectangular structure although it could be a square, rectangular or polygonal structure as well. In one preferred embodiment, the algae growing system would contain 96 trays and be approximately 42 feet in height.

The growth media may be pre-seeded with the specific organism to be propagated and introduced into the uppermost level of the stack. The stack, or group of stacks, is preferably sized to allow for the introduction of 100 percent of the new daily volume on a continuous basis in addition to the recycling of 33.3% of the output from the bottom of the stack for reseeding.

Carbon dioxide may be introduced continuously from the bottom of the stack as a minimum, and possibly at a multiplicity of locations in accordance with the specific needs of the specific strain of organism being grown.

Continuous monitoring of such items as pH, N, P, K, $CO_2$, O, H, pressure, temperature, and flow rates may be maintained on a continuous 24/7 basis for assurance of optimum growing and safety conditions.

A multiplicity of stacks may be maintained in a single large glass building.

A multiplicity of glass buildings may be located on 1 acre of land.

In one embodiment, a glass house would house approximately 50 stacks, wherein 6.3 of said stacks would be equivalent to 1 surface acre of pond. Therefore, each glass house would be the equivalent of approximately 7.94 acres of pond area.

In view of the foregoing, my invention relates to a vertical micro algal growing system wherein the apparatus consists of a closed environment formed by an enclosed structure housing a multiplicity of growing trays designed to minimize the footprint while maximizing the amount of growing area. The trays are designed and configured such that each tray has the optimum depth for maximum light penetration. The vertical micro algal growing system optimizes the absorption of introduced carbon dioxide. The vertical micro algal growing system is seeded from the top and is continuously harvested and reseeded while introducing the new nutrient growth media. Mirrored surfaces, e.g., Mylar or other light reflective surface, may be utilized to optimize exposure of the growing organisms to both natural and artificial light. The depth of the growing media may be controlled to optimize the combination of light, dark, nutrient and carbon dioxide as well as temperature for optimum, stable and predictable continuous growth and harvesting.

While the present invention has been described in the context of the embodiments illustrated and described herein, the invention may be embodied in other specific ways or in other specific forms without departing from its spirit or essential characteristics. Therefore, the described embodiments are to be considered in all respects as illustrative and not restrictive. The scope of the invention is, therefore, indicated by the appended claims rather than by the foregoing descriptions, and all changes that come within the meaning and range of equivalency of the claims are to be embraced within their scope.

What is claimed is:

1. An algae growing assembly for growing and cultivating algae, the algae growing assembly comprising:
    a plurality of growing trays vertically stacked together and removably retained within a transparent housing, wherein each growing tray is configured to flowingly transport nutrient enriched water to one of the plurality of growing trays positioned immediately beneath it;
    a plurality of lights positioned in between the plurality of growing trays and within the transparent housing;
    a carbon dioxide gas infusion system for adding carbon dioxide gas to the nutrient enriched water contained within each of the plurality of growing trays;
    characterized in that each of the plurality of growing trays is composed of a substantially planar rigid transparent plastic sheet having a substantially planar pliable transparent gas permeable membrane affixed on a top surface of the transparent plastic sheet, wherein the rigid transparent plastic sheet and the pliable transparent gas permeable membrane affixed thereon define, in the space between them, an inflatable carbon dioxide gas chamber that is configured to expand from essentially no volume to a substantially an expanded volume during gas inflation, and wherein the carbon dioxide gas infusion system is fluidicly connected to each of the plurality of growing trays such that carbon dioxide gas is able to (1) inflate substantially and expand the volume of the carbon dioxide gas chamber of each of the plurality of growing trays, and (2) diffuse into the nutrient enriched water contained within each of the plurality of growing trays;
    wherein each of the plurality of growing trays further comprises a spillway at one end, and wherein the plurality of growing trays are vertically stacked together such that the spillway of one of the plurality of growing trays is positioned opposite from the spillway of the one of the plurality of growing trays positioned immediately beneath it, thereby enabling the transport of the nutrient enriched water across the inflatable carbon dioxide gas chambers of each of the plurality of growing trays in a zigzag manner within the transparent housing.

2. The algae growing assembly of claim 1 wherein each of the plurality of growing trays further comprises one or more glue lines positioned along at least the outer edges of the pliable transparent gas permeable membrane and between the rigid transparent plastic sheet and the pliable transparent gas permeable membrane.

3. The algae growing assembly of claim 2 wherein the one or more glue lines define a serpentine path within the inflatable carbon dioxide gas chamber.

* * * * *